United States Patent [19]

Bailey, Jr.

[11] 4,169,664

[45] Oct. 2, 1979

[54] APPARATUS FOR DETERMINING PERIPHERAL VISION

[75] Inventor: Paul F. Bailey, Jr., 4885 NW. Barnes Rd., Portland, Oreg. 97210

[73] Assignee: Synemed, Inc., Berkeley, Calif.

[21] Appl. No.: 855,880

[22] Filed: Nov. 30, 1977

[51] Int. Cl.$^2$ .................... A61B 3/02; G02C 7/04
[52] U.S. Cl. .................... 351/23; 351/24; 351/36; 351/160 R
[58] Field of Search .................... 351/23, 24, 30, 36, 351/6, 7, 160, 16; 350/96.24

[56] References Cited

U.S. PATENT DOCUMENTS

| 3,780,979 | 12/1973 | de Guillebon | 351/16 |
| 4,063,807 | 12/1977 | Gelius et al. | 351/24 |

FOREIGN PATENT DOCUMENTS 1335980  12/1963  France ................................ 351/24

Primary Examiner—John K. Corbin
Assistant Examiner—Rodney B. Bovernick
Attorney, Agent, or Firm—Kolisch, Hartwell, Dickinson & Stuart

[57] ABSTRACT

An apparatus for use in determining the peripheral vision extent of a patient's eye includes a contact lens type construction detachably fitted to the eye having multiple optical fibers each extending to an illuminating source. Upon illumination of a selected fiber, light is directed into the eye and the patient's response noted. The fibers are distributed so as to extend radially outwardly on the lens and thus a patient's responses provide a so-called "map" of peripheral vision extent.

16 Claims, 4 Drawing Figures

U.S. Patent
Oct. 2, 1979
4,169,664
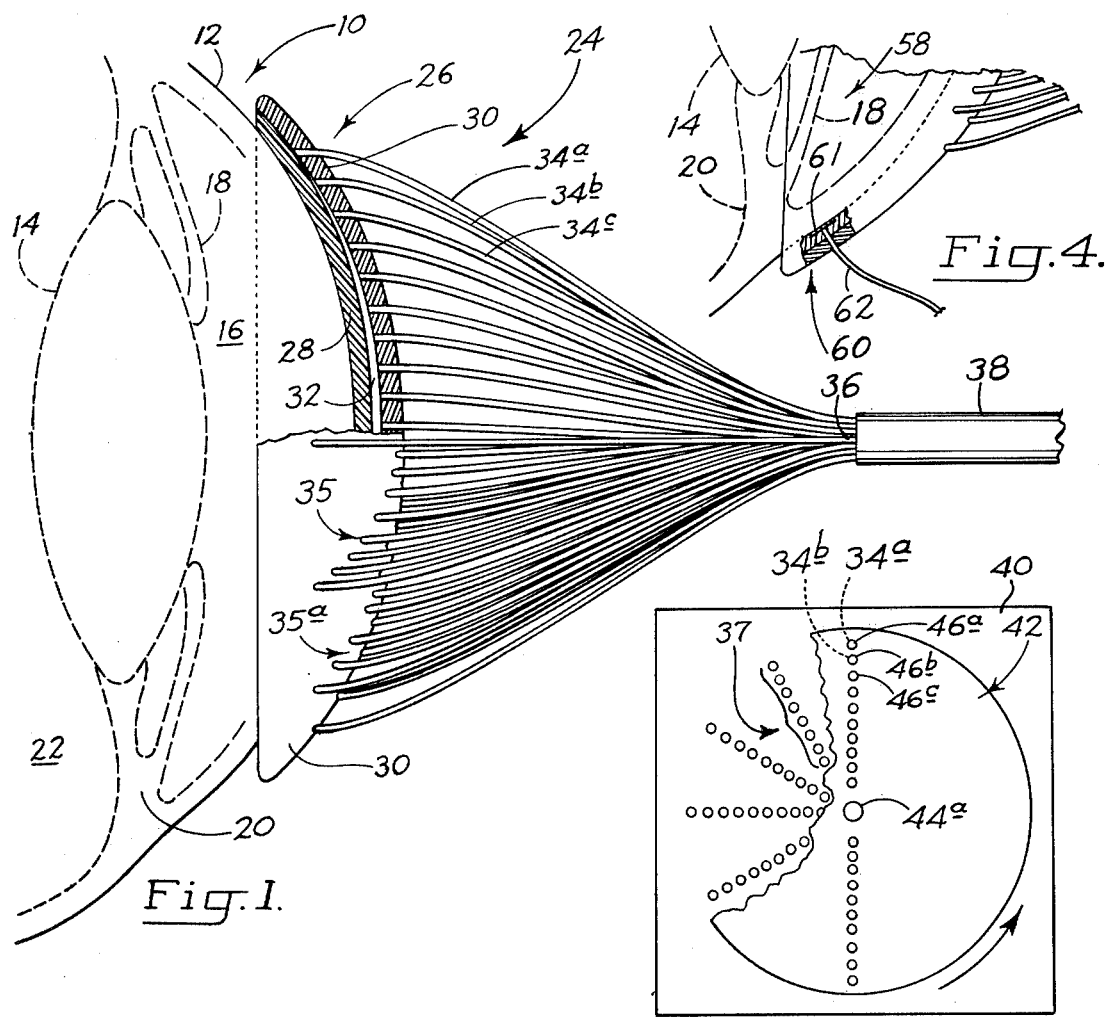
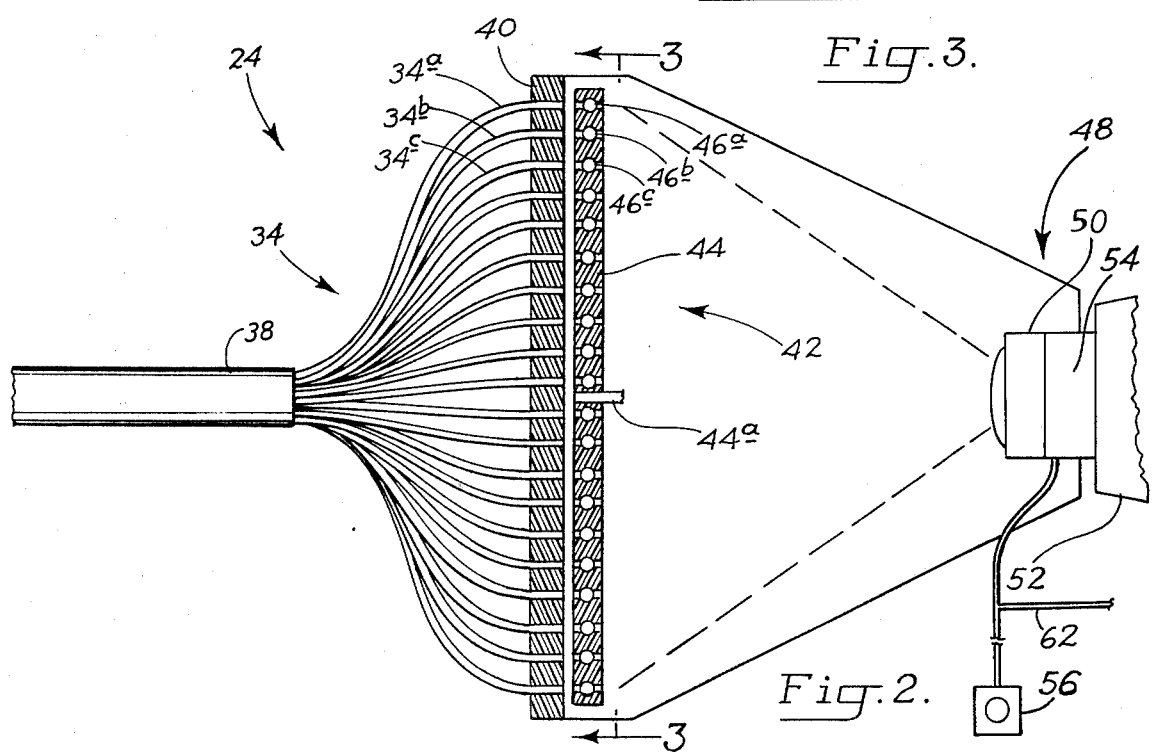

APPARATUS FOR DETERMINING PERIPHERAL VISION

BACKGROUND AND SUMMARY OF THE INVENTION

The present invention relates to ophthalmology, and more particularly to apparatus including a contact lens type construction which may be fitted on the eye including means for directing light thereinto so that a patient's peripheral vision extent can be measured.

In a typical eye examination, several tests may be conducted in order to determine the visual efficiency of a patient's eyes. One test often conducted is to determine the peripheral vision extent of the eyes. Typically, an ophthalmologist will move a point source of light from adjacent the side of a patient's head forwardly until the patient indicates that the light is seen. The light source used in such a test is, for example, an ophthalmoscope used by the doctor conducting the test.

A problem with the above-described peripheral vision test resides in the fact that the usual patient is aware that a point source of light will soon be within view, and therefore, the patient will tend to automatically shift the eyeball to view the light source. Of course, when such eyeball shifting occurs, the patient's peripheral vision extent is not being accurately measured. Some patients can be sufficiently trained to continuously maintain their eyes looking directly forwardly, but other patients simply cannot be so trained.

Another problem resulting from the use of a hand-held point source of light to determine peripheral vision resides in the fact that it is difficult to determine the exact location on the eye which responds to the light source.

With the above problems in mind, it is a general object of the present invention to provide an apparatus for accurately determining peripheral vision extent irrespective of shifting of the eye. More particularly, the present invention contemplates the use of a contact lens type construction to which are connected a plurality of optical fibers. The fibers are distributed over the area bounded by the periphery of the lens so as to extend through the lens at discrete locations thereon. The fibers may be selectively illuminated so that light will be directed into the eye. It can be appreciated that a patient's response to the illumination of a particular fiber would be independent of the positioning of the eye because the lens rides with the eye.

Another object of the present invention is to provide a simple and efficient light producing means for selectively illuminating each of the optical fibers. Additionally, it is desirable to selectively regulate the intensity of the light being directed into the eye.

These and additional objects and advantages of the present invention will be more readily understood from a consideration of the drawings and the detailed description of the invention.

BRIEF DESCRIPTION OF THE DRAWINGS

FIG. 1 is a cross-sectional side view of an eye to which is fitted a contact lens type construction having optical fibers according to the present invention, the lens being partially shown in cross section and the fibers being broken along their lengths at the right;

FIG. 2 is a cross-sectional viewing of an extension to the right of the optical fibers shown in FIG. 1 and illustrates mounting of the optical fibers so that they may be selectively illuminated by individual light producing elements; and FIG. 3 is a view taken along lines 3—3 of FIG. 2 and illustrates a rotatable member or disc, partially broken away, on which the light producing elements are mounted; and FIG. 4 is a partial view, similar to that of FIG. 1, showing an embodiment for enabling pupil response to be recorded.

DETAILED DESCRIPTION OF THE INVENTION

Turning now to the drawings, and referring particularly to FIGS. 1 and 2, there is indicated generally at 10 an eyeball, shown in a cross-sectional side view, the cornea being shown at 12 and the lens at 14. The anterior chamber is shown at 16, the iris at 18 and the ciliary body at 20. Only a portion of the vitreous body is shown at 22.

FIGS. 1 and 2 are to be viewed together, with FIG. 2 being an extension to the right of FIG. 1. As shown in FIG. 1, an apparatus according to the present invention is generally indicated at 24. Generally indicated at 26 is a contact means or contact lens type construction which includes joined first and second cup-shaped members 28 and 30, respectively. Member 28 is formed with a concave inner surface for detachable fitting on cornea 12. Member 30 is mounted on member 28 and the members are configured so that a resolution space 32 exists between the adjacent portions of their surfaces. Member 30 is constructed of nontransparent material or has a nontransparent outer surface.

Extending through the thickness of member 30 at discrete locations thereon are the ends of multiple optical fibers generally indicated at 34. As can be seen from a consideration of the nonbroken away portion of contact means 26, optical fibers 34 are distributed over the area bounded by the periphery of contact means 26 and extend radially outwardly from the central axis of contact means 26. Individual optical fibers are shown at 34a, 34b, etc. A plurality of radially extending fiber rows are provided, two of which are indicated generally at 35 and at 35a.

Optical fibers 34 are bundled together at the right of contact means 26 as shown at 36 and are extended through a supporting guide 38. Guide 38 is provided to group fibers 34 in a compact arrangement for extending them to an illuminator means, described later.

With reference directed now particularly to FIG. 2, it can be seen that optical fibers 34 extend through guide 38 and are mounted with their opposite ends supported in rows in a support structure 40. As shown in FIG. 2, for purposes of clarity, only one row consisting of twenty optical fibers is illustrated.

An illuminator means for illuminating optical fibers 34 is generally designated at 42 and includes a rotatable member such as disc 44 provided with a plurality of discrete light-producing elements indicated at 46a, 46b, 46c. Optical fibers 34 and illuminator means 42 define a so-called light emitting means. Light producing elements 46a, 46b, etc. are separated from one another in a continuous diametrical row as can be seen in FIG. 3. Light producing elements 46a, 46b, etc. may be light-emitting diodes or other light producing means which may be selectively actuated. Disc 44 is connected to a rotatable shaft 44a so that light-producing elements 46a, 46b, etc. may be rotated relative to structure 40. The mounting and drive for shaft 44a is not shown.

It should be noted from a consideration of FIG. 2 that elements 46a, 46b, etc. are spaced apart from each other a distance substantially equal to the spacing of optical fibers 34 mounted in structure 40. As shown in FIGS. 2 and 3, the righthand ends of optical fibers 34 are distributed over structure 40 so as to extend radially outwardly from the axis of shaft 44a in separate rows corresponding generally to the row pattern on member 30. Thus, it can be appreciated that each of the light producing elements 46a, 46b, etc. can be selectively aligned with selected ones of the optical fibers such as individual fibers 34a, 34b, etc. shown in FIG. 2.

Still considering FIG. 2, there is shown to the right of disc 44 a recording means generally designated at 48. Recording means 48, as shown, includes a camera 50 positioned for recording an image of elements 46a, 46b, etc. on rotatable member 42. A programmed means 52 is suitably connected to shaft 44a and elements 46a, 46b, etc. and is operable for initiating illumination of a selected element, varying its intensity and rotating disc 44. Various operations and sequences may be provided by programmed means 52 depending upon testing requirements. Of course, programmed means 52 may be provided with suitable means so that a doctor may independently control optical fiber selection, intensity and rotation of disc 44. Additionally, a camera control 54 is interposed between camera 50 and programmed means 52 for operating the camera upon manual actuation by a patient of a push buttom device indicated at 56.

Operation of apparatus 24 in determining peripheral extent of a patient's eye will now be described. Contact means 26 is fitted on an eye and disc 44 is positioned so that light producing elements 46 are aligned with a selected row of optical fibers. For example, as shown in FIGS. 2 and 3, light producing elements 46a, 46b, etc. are aligned with the right hand end of optical fibers 34a, 34b, etc. Upon actuation of element 46a by programmed means 52, optical fiber 34a will be illuminated and transmit light to the left hand end thereof. The light will thereby be directed into the patient's eye. If the patient can visualize the light, he is instructed to depress push button device 56 so that camera 50 will record which element has been illuminated, its intensity and the position of disc 44. If the patient cannot visualize the light, a succeeding fiber such as fiber 34b will be illuminated. Likewise, successive ones of the fibers may be sequentially illuminated to test a patient's peripheral vision. The camera will keep a permanent record of the patient's responses. Programmed means 52 may also be provided with the capability to successively illuminate the fibers and rotate disc 44 upon receiving a signal from the patient that a light was visualized. The operation of camera 50 could be coordinated by use of programmed means 52 if desired.

Further, it is to be noted that light producing elements 46a, 46b, etc. are provided with means for regulating light intensity. Thus, if a certain intensity produced by element 46a could not be visualized by the patient, a higher intensity may be provided for testing purposes. It can be appreciated that any desired sequence and intensity could be employed for testing. For instance, programmed means 52 could be programmed to selectively sequence and actuate any preselected element 46a, 46b, etc. in any desired order.

After a test has been performed with respect to one row of optical fibers, disc 44 is rotated (for example, to the left in FIG. 3) so that elements 46a, 46b, etc. are aligned with the next row for selective fiber illumination. As shown in FIG. 3, the next row is indicated at 37. In a like manner, elements 46a, 46b, etc. are aligned with successive rows and the elements are actuated for illuminating the optical fiber aligned therewith. At completion of the test, it can be appreciated that a so-called "map" of the peripheral vision extent of a patient will be constructed and recorded by camera 50 and programmed means 52. This map can then be used for diagnostic purposes.

It is also to be noted that pupil response to light stimuli may be recorded irrespective of whether or not the patient can consciously perceive the stimuli. By way of example, as shown in FIG. 4, a somewhat larger contact means 58 is provided with an iris myrograph indicated at 60. Iris myrograph 60 includes a conducting element 61 mounted on the contact means for positioning against the cornea adjacent to the muscle which controls pupil opening. Element 61 is also connected via lead 62 to camera control 54. Thus, camera 50 will be automatically actuated by a means which is sensitive for detecting rather minute pupil responses to light stimuli.

There are several important advantages which result from the construction of the present invention. First of all, it can be seen that it is not necessary for a patient to continuously maintain his eyeball from shifting during a peripheral vision test. Because contact means 26 rides with movement or shifting of the eyeball, the extent of peripheral vision can still be measured irrespective of eyeball position. Thus, those patients who cannot be trained to not shift their eyes could have their peripheral vision accurately mapped. Another advantage of the present invention resides in the fact that an exact knowledge of the location of the end of the optical fibers are known with respect to contact means 26. Therefore, when a patient indicates that a light is seen, the precise location on his eyeball which corresponds to his peripheral vision is determined.

Although the invention has been described with reference to particular preferred embodiment, changes and modifications will be apparent to those skilled in the art in view of the foregoing description which is intended to be illustrative and not limiting the invention defined in the appended claims.

It is claimed and desired to secure by Letters Patent:

1. Apparatus for use in determining the peripheral vision extent of an eye comprising:
    contact means for detachable fitting on the cornea; and
    light emitting means operable for selectively directing light into the eye including multiple optical fibers distributed over the area bounded by the periphery of said contact means at discrete locations radially spaced from the central axis of said contact means.

2. The apparatus of claim 1, wherein at least a portion of said contact means is nontransparent.

3. The apparatus of claim 1 further including an illuminator means, each of said fibers having one end connected to said contact means and the other end disposed adjacent said illuminator means.

4. The apparatus of claim 3, wherein said illuminator means is operable for selectively illuminating a preselected fiber.

5. The apparatus of claim 4, wherein said illuminator means is operable for selectively regulating light intensity in an illuminated fiber.

6. The apparatus of claim 5, wherein said illuminator means includes multiple light producing elements, each being selectively positionable for illuminating preselected ones of said fibers.

7. The apparatus of claim 6, wherein recorder means are provided for recording fiber illumination.

8. Apparatus for use in determining the peripheral vision extent of an eye comprising:
   contact means for detachable fitting on the cornea;
   multiple optical fibers each having one end connected to said contact means, said fibers being distributed over the area bounded by the periphery of said contact means at discrete locations radially spaced from the central axis of said contact means; and
   illuminator means including a plurality of selectively operable light producing elements for illuminating preselected ones of said fibers.

9. The apparatus of claim 8, wherein said contact means includes a first member having a generally concave surface for accommodating the eye's curvature and a second member mounted on said first member.

10. The apparatus of claim 9, wherein said members have at least a portion of their adjacent surfaces spaced apart.

11. The apparatus of claim 10, wherein said optical fibers are connected to said second member.

12. The apparatus of claim 11, wherein at least a portion of said second member is nontransparent to external light.

13. The apparatus of claim 8 wherein said light producing elements are each selectively positionable for illuminating preselected ones of said fibers.

14. The apparatus of claim 13, wherein each of said light producing elements is operable for selectively regulating light intensity in a fiber illuminated by it.

15. The apparatus of claim 14 wherein an iris myrograph is provided on said contact means for detecting pupil responses to an illuminated one of said fibers.

16. The apparatus of claim 8 wherein said fibers are connected to said contact means in a plurality of rows which extend radially from the central axis of said contact means.

* * * * *